US010324035B2

(12) United States Patent
Patterson et al.

(10) Patent No.: US 10,324,035 B2
(45) Date of Patent: Jun. 18, 2019

(54) NONDESTRUCTIVE OPTICAL TESTING SYSTEMS AND RELATED METHODS FOR PREDICTING MATERIAL FAILURE

(71) Applicant: BRIGHAM YOUNG UNIVERSITY, Provo, UT (US)

(72) Inventors: James E. Patterson, Orem, UT (US); Shawn Christopher Averett, Orem, UT (US)

(73) Assignee: BRIGHAM YOUNG UNIVERSITY, Provo, UT (US)

( * ) Notice: Subject to any disclaimer, the term of this patent is extended or adjusted under 35 U.S.C. 154(b) by 0 days.

(21) Appl. No.: 15/305,836

(22) PCT Filed: Jul. 13, 2015

(86) PCT No.: PCT/US2015/040226
§ 371 (c)(1),
(2) Date: Oct. 21, 2016

(87) PCT Pub. No.: WO2016/010933
PCT Pub. Date: Jan. 21, 2016

(65) Prior Publication Data
US 2017/0045449 A1   Feb. 16, 2017

Related U.S. Application Data

(60) Provisional application No. 62/023,986, filed on Jul. 14, 2014.

(51) Int. Cl.
*G01N 21/88* (2006.01)
*G01N 21/63* (2006.01)
(Continued)

(52) U.S. Cl.
CPC ....... *G01N 21/636* (2013.01); *G01N 21/8806* (2013.01); *G01N 21/95* (2013.01); *G01N 2021/8472* (2013.01); *G01N 2201/08* (2013.01)

(58) Field of Classification Search
CPC .. G01N 21/636; G01N 21/8806; G01N 21/95; G01N 2021/8472;
(Continued)

(56) References Cited

U.S. PATENT DOCUMENTS 5,557,409 A     9/1996  Downer et al.
5,706,088 A *   1/1998  Chao ................. G01N 21/211
                                                    356/369
(Continued)

OTHER PUBLICATIONS

Pedersen, et al., (1988) Nonlinear optical methods in the nondestructive testing of metal surfaces. NDT International vol. 21, No. 6, 411-414.
(Continued)

*Primary Examiner* — Isiaka O Akanbi
(74) *Attorney, Agent, or Firm* — Dorsey & Whitney LLP

(57) ABSTRACT

Embodiments disclosed herein relate to systems and methods for nondestructive testing of material to predict oncoming failure thereof. For example, components and/or elements of various devices may be nondestructively tested to predict and/or prevent failure of such components and elements during operation. In some embodiments, the components and/or elements may be tested without removal thereof from systems or devices (e.g., a wing of an airplane may be tested for oncoming failure without removing the wing from the airplane).

21 Claims, 3 Drawing Sheets

(51) Int. Cl.
*G01N 21/84* (2006.01)
*G01N 21/95* (2006.01)

(58) Field of Classification Search
CPC .. G01N 2203/0212; G07C 3/00; G01B 11/30; G01B 11/24; G01B 11/303
USPC ........... 356/445–448, 237.2–237.6, 600–624
See application file for complete search history.

(56) References Cited

U.S. PATENT DOCUMENTS

| | | | | |
|---|---|---|---|---|
| 5,757,496 A * | 5/1998 | Yamazaki | ............ | G01B 11/303 356/600 |
| 5,835,220 A * | 11/1998 | Kazama | ................... | G01J 4/04 356/237.2 |
| 6,636,310 B1 * | 10/2003 | Ben-Dov | ................ | G01B 11/24 356/601 |
| 6,943,353 B2 | 9/2005 | Elmore et al. | | |
| 7,433,056 B1 * | 10/2008 | Janik | ................. | G01B 11/0616 356/301 |
| 2001/0028460 A1 * | 10/2001 | Maris | ................. | G01N 21/1702 356/432 |
| 2008/0101657 A1 * | 5/2008 | Durkin | ..................... | G01J 3/02 382/110 |
| 2009/0018415 A1 * | 1/2009 | Robinson | ........... | A61B 5/14558 600/310 |
| 2011/0060568 A1 | 3/2011 | Goldfine et al. | | |
| 2013/0301042 A1 * | 11/2013 | Urano | ................ | G01N 21/9501 356/237.5 |
| 2014/0253912 A1 * | 9/2014 | Honda | ................. | G01N 21/956 356/237.5 |
| 2016/0131594 A1 | 5/2016 | Koldiaev et al. | | |

OTHER PUBLICATIONS

Ying, et al., (2000) Nondestructive evaluation of incipient corrosion in a metal beneath. Optics Letters vol. 25, No. 16, 1189-1191.
International Search Report and Written Opinion from International Application No. PCT/US2015/040226 dated Oct. 13, 2015.
"Harmonic F Series Metrology System", http://www.femtomitrix.com/ last accessed Mar. 22, 2018, 5 pages.

* cited by examiner

NONDESTRUCTIVE OPTICAL TESTING SYSTEMS AND RELATED METHODS FOR PREDICTING MATERIAL FAILURE

CROSS-REFERENCE TO RELATED APPLICATIONS

This application claims priority to U.S. Provisional Application No. 62/023,986 filed on 14 Jul. 2014, the disclosure of which is incorporated herein, in its entirety, by this reference.

BACKGROUND

Generally, predicting fatigue and failure of components has various commercial applications. For example, when a test can accurately predict oncoming and/or imminent failure of components, such components may be removed from service and/or replaced before the failure (e.g., during routine maintenance), thereby avoiding stoppage time, increasing safety, etc., of the devices and systems that include such components.

In some instances, testing may involve damaging and/or destroying the components being test. However, such testing may not be practical because the tested component may not be placed back into service and will have to be replaced due to damage and/or destruction.

Accordingly, users and manufacturers of nondestructive testing equipment continue to seek improvements thereto.

SUMMARY

Embodiments disclosed herein relate to systems and methods for nondestructive testing of material to predict oncoming failure thereof. For example, components and/or elements of various devices may be nondestructively tested to predict and/or prevent failure of such components and elements during operation. In some embodiments, the components and/or elements may be tested without removal thereof from systems or devices (e.g., a wing of an airplane may be tested for oncoming failure without removing the wing from the airplane).

In an embodiment, a nondestructive material testing system is disclosed. The nondestructive material testing system includes a light source configured to emit predominantly a first frequency light and configured to irradiate a portion of a surface of a test body at a first location. The nondestructive material testing system also includes a light detector positioned and configured to detect an intensity of a second frequency light that is emitted from the test body in second harmonic generation responsive to the first frequency light. Furthermore, the nondestructive material testing system includes a controller coupled to the light detector and configured to: (i) receive one or more first signal values from the light detector, the one or more signal values corresponding to amount of the second frequency light detected by the light detector from the test body; and (ii) output one or more of a probability of failure of the test body under operating conditions at least partially based on the one or more first signal values or a recommendation on placing the test body into service.

Embodiments also include a nondestructive material testing system that includes a light source positioned at a first location and configured to emit predominantly a first frequency light and further configured to irradiate a portion of a surface of a test body. The nondestructive material testing system further includes a light detector positioned and configured to detect an intensity of a second frequency light that is emitted from the test body in second harmonic generation responsive to the first frequency light. Moreover, the nondestructive material testing system includes a controller coupled to the photodetector and configured to: (i) receive a first signal value from the light detector at a first test; (ii) receive a second signal value from the light detector at a second test; and (iii) determine one or more of a probability of failure of the test body under operating conditions or a recommendation on placing the test body into service based at least partially on a difference between the first signal value and the second signal value.

In an embodiment, a method for predicting failure of a test body under operating conditions is disclosed. The method includes irradiating a surface of a test body at a first location with predominately a first frequency light for a first test, and detecting a first intensity of a second frequency light generated by the test body in second harmonic generation for the first test. The method further includes irradiating the surface of the test body at a second location with predominately the first frequency light for a second test, and detecting a second intensity of the second frequency light generated by the test body in second harmonic generation for the second test. Additionally, the method includes, at a controller, correlating a change between the first intensity and the second intensity to output one or more of a probability of failure of the test body under the operating conditions or a recommendation on placing the test body into service.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments, wherein identical reference numerals refer to identical or similar elements or features in different views or embodiments shown in the drawings.

DETAILED DESCRIPTION

Figure 1:
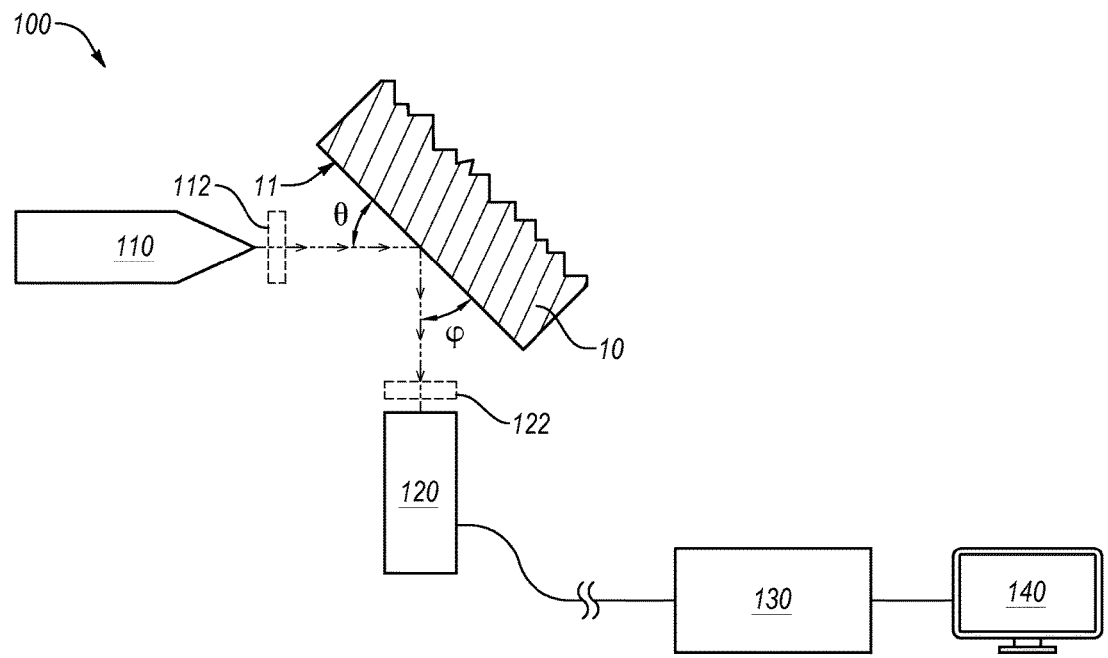
FIG. 1 illustrates a nondestructive testing system according to an embodiment.

Embodiments disclosed herein relate to nondestructive testing systems and methods for nondestructive testing of material to predict oncoming failure thereof. For example, components and/or elements of various devices may be nondestructively tested to predict and/or prevent failure of such components and elements during operation. In some embodiments, the components and/or elements may be tested without removal thereof from systems or devices (e.g., a wing of an airplane may be tested for oncoming failure without removing the wing from the airplane).

In some embodiments, the component or element of interest (e.g., a test body) may be tested in an initial condition (e.g., in a first test) and in a subsequent condition (e.g., in a second test). For example, in the first and second tests, a surface of the test body may be exposed to or irradiated with light to produce second harmonic generation ("SHG") light from the test body, which may be received at a light detector (e.g., the location(s) on the surface of the test body that is irradiated in the first and second tests may be generally the same or may be different, such as to minimize damage to the test body from the light). More specifically, the signals received from the light detector at a controller during the first test may be compared to the signals received therefrom during the second test to evaluate or determine onset of failure of the test body.

As described below in more detail, the light impinged onto the surface of the test body may have a first frequency and corresponding wavelength (e.g., the peak or dominant intensity of the light may be concentrated around 550 nm wavelength, another suitable visible wavelength of about 390 nm to about 700 nm, or other suitable wavelength), and the light generated by the test body may have a second frequency that corresponds to the second harmonic generation effect (e.g., the second frequency may be double the first frequency or ½ of the first wavelength). For example, the test body may be irradiated with about 550 nm light (e.g., green light), and the second harmonic generation light received at the light detector may be about 275 nm light (e.g., ultraviolet light). In an embodiment, the controller may be configured (e.g., programmed) to compare the signals received from the light detector during the first test (e.g., signals related to the intensity of the second frequency light from the test body) to the signals received during the second test to determine the change or difference therebetween that may correspond to onset of failure of the test body.

In some embodiments, the first test may be performed before placing the test body into service or operation (e.g., on an unused component or element). The second test may be performed after the test body has been in operation (e.g., after the component has been subject to operating stress. The controller may determine whether the test body should be taken out of service (e.g., due to high risk of failure during operation).

Additionally or alternatively, the nondestructive testing system may determine relief of stress in a test body. For example, a test body subjected to the first test may have a relatively high level of residual stresses and/or dislocations (e.g., in a crystalline test body, such as generally single crystal or polycrystalline test body) at or near the surface thereof. After the first test, the test body may be subjected to a stress relief treatment, such as annealing. The second test may be performed after relieving stress, and the system may determine whether the stress relieving operation suitably or successfully relieved stress.

In some embodiments, the controller may determine that a change or difference between signals received during the first test and the second test is related to a change in material structure of the test body. For example, the controller may determine that the change in signal from the first test to the second test is related to precipitation of a specific material phase at grain boundaries of the base material (e.g., precipitation of magnesium aluminide, such as beta phase ($Mg_2Al_3$), from an aluminum-magnesium alloy). Moreover, the controller may determine that the tested component (or test body) should be taken out of service due to corrosion or unsuitably high levels of separation of materials in the bulk of the test body.

FIG. 1 illustrates a nondestructive testing system 100 according to an embodiment. More specifically, the nondestructive testing system 100 includes a light source 110 (e.g., a monochromatic or substantially monochromatic light source, such as a laser), which may emit and direct light at and to a surface of test body 10, and a photodetector or light detector 120 (e.g., a photomultiplier tube, one or more photodiodes, or an array of photodiodes) that may detect a light emitted from the test body 10. The light detector 120 may be coupled to one or more controllers, such as to controller 130 that may receive signals from the light detector 120 that correspond with detection of light or photons thereby (e.g., the signals received from the light detector 120 may correspond to an intensity or amount of light (or quantity of photons) entering the light detector 120). The light detector 120 and controller 130 may be directly or indirectly electrically connected or wired together. Alternatively or additionally, the light detector 120 and controller 130 may be connected over a wireless connection.

In an embodiment, the nondestructive testing system 100 may include one or more optical elements (e.g., optical element 122), such as optical filter(s) in the path of light between the surface of the test body 10 and the light detector 120. For example, as described above, the light source 110 may emit a predominately first frequency or wavelength light, and the test body 10 may generate the first frequency light and a second frequency light, where the second frequency light is generated as a result of second harmonic generation. In some embodiments, the optical filter(s) may filter some, most, or substantially all of the light that is not second frequency light (e.g., filter out substantially all of the first frequency light).

In some embodiments, the nondestructive testing system 100 may include one or more optical elements (e.g., optical element 112) in the path of light emitted from the light source 110. For example, the optical element 112 may include one or more lenses configured to focus the light on the surface of the test body 10, the optical element 112 may include one or more optical polarizing filters configured to filter light to a substantially single polarization, etc. In any event, the light impinging onto the surface of the test body 10 may be conditioned and/or the light emitted from the test body 10 may be conditioned before reaching the light detector 120.

In some embodiments, the controller 130 may filter the signal(s) received from the light detector 120 (e.g., to compensate for the light received by the light detector 120 from the surrounding environment). For example, the controller 130 may first receive baseline signal(s) from the light detector 120 without irradiating the test body 10 with the first frequency light from the light source 110. Subsequently, when testing the test body 10, the signal(s) received from the light detector 120 while the test body 10 is irradiated with the first frequency light from the light source 110, the controller 130 may filter out the baseline signal(s) from the signal(s) received in the test.

As described above, the light from the light source 110 may be directed and/or projected onto a surface of the test body 10, such as test surface 11. In some instances, the test surface 11 may be generally planar. It should be appreciated, however, that the test surface 11 may have any shape, curvature, size, etc. Moreover, a small portion of the test surface 11 that is subjected to the light from the light source 110 may be approximated as a planar segment of the test surface 11 (e.g., a circumference of 25 µm). Generally, the light from the light source 110 may impinge onto the test surface 11 at any suitable angle relative thereto. For example, the light may impinge onto the test surface 11 at angle θ (e.g., at 30°, 45°, at 60°, etc.). Furthermore, the light detector 120 may be oriented relative to the test surface 11 in order to receive the light generated at the test body 10 (e.g., the light emitted from the test body 10 may be emitted at the same angle relative to the test surface 11 as the incident light impinging on the test surface 11 from the light source 110, such as 45°).

In some embodiments, the angles of light source 110 and/or light detector 120 may be adjusted relative to the test surface 11 (e.g., the second harmonic generation light emitted from the test body 10 may be oriented at angle φ, which may be approximately the same as the angle θ of the incident light emitted from the light source 110). For example, the angle of the light source 110 and/or light detector 120 may be adjusted relative to the test surface 11 to improve generation of the second harmonic generation and/or that amount of light produced in second harmonic generation from the test body 10. In some embodiments, orienting the light source 110 to emit light at 45° relative to the test surface 11 may improve and/or maximize the amount of light produced in second harmonic generation from the test body 10 (e.g., the incident light and the light produced and second harmonic generation from the test body 10 may be at approximately 90° relative to each other).

As described above, the controller 130 may be operably coupled to the light detector 120 and may receive signals therefrom. More specifically, for example, the signals received from the light detector 120 may correspond to the amount of light received at the light detector 120. For example, the light detector 120 may receive the second frequency light, while the first frequency light and/or other light may be filtered out. Hence, the signal received from the light detector 120 at the controller 130 may correspond to the amount of second frequency light produced from the test body 10 in second harmonic generation (e.g., intensity of the signal, such as amperage of current generated at the light detector 120, received or detected at the controller 130 from the light detector 120 may be related to or based on the amount of light received at the light detector 120).

The controller 130 may correlate the intensity of the signal received from and/or the amount of second frequency light detected by the light detector 120 to a state of fatigue and/or strain (or deformation) of the test body 10. In particular, for example, the controller 130 may determine if and/or when the test body 10 should be taken out of service due to a likelihood of failure during operation. For example, as a result of loading, the test body 10 may develop one or more of micro-cracks (e.g., at the test surface 11), concentrated regions of high dislocation density, or may exhibit fatigue that may result in sudden failure of the test body 10 during operation. That is, one or more of micro-cracks, high dislocation densities, or visible signs of material fatigue (e.g., change of color on a portion of the test surface 11 of the test body 10) may indicate that continuing use of the test body 10 in operation may result in sudden failure. The controller 130 may determine onset of the micro-cracks before the micro-cracks extend to or are detectable on the test surface 11 of the test body 10 via other nondestructive testing such as visual inspection, magnetic particle inspection, or ultra-sound inspection. Furthermore, the controller 130 may determine the onset of fatigue before the visible signs of fatigue appear on the test surface 11. Hence, the test body 10 may be taken out of service and/or replaced before failure thereof during operation.

In some embodiments, the controller 130 may include a processor, memory coupled to the processor, an input/output interface coupled to the processor, and a power supply coupled to the processor. In at least one embodiment, the controller 130 may be a computer (e.g., programming instructions may be stored in memory of the computer and may control operation thereof as described herein). Alternatively, the controller 130 may be a computer (e.g., the programming instructions may be included on programmable gate arrays, such as field-programmable gate arrays ("FPGAs")).

In some embodiments, the controller 130 may store (e.g., in memory) data related to the signals received from the light detector 120 when testing sample or control bodies with known strain and/or fatigue states (e.g., during calibration testing). For example, calibration of the controller 130 may be performed by testing samples that have been previously strained (e.g., loaded and/or cycled to have a known amount of strain). Also, the test samples may be analyzed to determine the amount of strain therein (e.g., the test samples may be analyzed via x-ray diffraction or other suitable analytical technique, etc.). Moreover, in some embodiments, the test samples may be destructively tested (e.g., after calibration testing thereof) to determine the failure point, such as the number of cycles to failure, maximum load to failure, etc.

Hence, in some embodiments, the controller 130 may include calibration data that relates signal values or signal value ranges to corresponding strain or fatigue state of specific materials. Moreover, the calibration data may include corresponding surface finishes of the calibration test bodies that were tested during calibration of the controller 130. In at least one embodiment, the calibration data stored at the controller 130 may include surface roughness data that corresponds with the tested calibration samples.

The controller 130 also may include threshold values related to failure that correspond with the strain and/or fatigue states of test bodies, such as test body 10. For example, a user may provide one or more threshold values related to strain of the material, residual stresses, number of loading cycles to failure, etc. (e.g., which may be stored at the controller 130 in memory), which may be correlated to corresponding calibration data (e.g., to calibration signal values received during calibration of the controller 130) to produce signal threshold values and/or threshold ranges. In an embodiment, the controller 130 may provide an alert or indicate that the state of test body 10 exceeds one or more threshold values and/or that the test body 10 should be taken out of service.

As described above, when the light detector 120 receives the second frequency light that is generated by test body in response to irradiation thereof with the first frequency light from the light source 110, the signal generated by the light detector 120 and received or detected by the controller 130 may be processed at the controller 130 to determine whether the test body 10 should be removed from service (e.g., based on one or more parameters, such as strain or fatigue threshold values). For example, the controller 130 may compare the signal value received from the light detector 120 during testing of the test body 10 to the signal values stored at the controller 130 from the calibration tests (described above) to determine whether the test body 10 is experiencing onset of fatigue and/or relatively high strain (e.g., whether the determined strain or level of fatigue is at a threshold level). In an embodiment, the threshold levels (as mentioned above) may be entered by a user at the controller 130 (e.g., over the input/output interface, such as from a keyboard coupled to the controller 130 at the input/output interface).

In some embodiments, specific threshold levels may be stored at the controller 130 for specific materials, components, shapes, surface finishes, combinations of the foregoing, etc. (e.g., the controller 130 may receive threshold data from a user). Furthermore, various threshold levels may correspond to various indication or recommendation outputs generated by the controller 130. For example, when the stress or strain is at or near a specific threshold value or within a range of threshold values, the controller 130 may provide one or more corresponding indications or recommendations (e.g., to repeat test within T period of time, to monitor operation of the test body, to remove and/or replace or repair the test body, etc.). Additionally, when the strain and/or fatigue of the test body 10 is below the threshold value(s), the controller 130 may provide an indication that the test body 10 may be placed back into service. In any event, the controller 130 may provide an indication of whether the test body 10 may be placed back into service, which may be based at least in part on the signal(s) received from the light detector 120.

In some embodiments, the signal(s) received from the light detector 120 at the controller 130 may be correlated with concentration(s) of dislocation density on or near the surface (e.g., for crystalline materials) and/or correlated with molecular changes or structures (e.g., crazing in polymers or shear bands, or strain localization in amorphous materials such as metallic glasses). For example, the controller 130 may be calibrated by sampling calibration test bodies with known dislocation densities (or determining the dislocation densities after calibration sampling or testing) and storing at the controller 130 the values of the corresponding signals received from the light detector 120. In any event, the controller 130 may include calibration data or values of dislocation densities correlated with signals received from the light detector 120 for specific materials and surface finishes tested during calibration of the controller 130. Moreover, the controller 130 may correlate the dislocation densities and/or changes therein with the strain or fatigue state of the test body 10 and may generate a corresponding recommendation related to further use of the test body 10 in service (e.g., as described above).

In at least one embodiment, the controller 130 may be calibrated to determine onset of fatigue or the oncoming failure of an amorphous material. For example, the controller 130 may be calibrated by testing one or more calibration test bodies with known fatigue or strain states (which may be determined before or after the calibration testing) and storing the strain and/or fatigue levels together with corresponding signals received from the light detector 120 in calibration testing. Subsequently, signals received at the controller 130 from the light detector 120, in tests of the test body 10 that includes amorphous material, may be correlated with the fatigue and/or strain levels of the test body 10. Moreover, the controller 130 may provide an output and/or recommendation related to further use of the test body 10 in service, which may be at least in part based on the determined fatigue and/or strain levels as well as on the threshold fatigue and/or strain values (e.g., as described above).

Generally, the test body 10 may include any number of suitable materials, which may be amorphous or crystalline. Hence, the nondestructive testing system 100 may determine onset fatigue or failure of the test body 10 that includes any number of materials. In some applications, the test body 10 may include a metallic alloy, such as aluminum alloy (e.g., 5000 series aluminum alloy including aluminum and magnesium), which may be susceptible to precipitation of certain intermetallic compound(s) at or near the grain boundaries thereof that can contribute or cause intergranular corrosion or stress corrosion cracking, thereby compromising the structural integrity of the test body 10. In other embodiments, the test body 10 may include a single-crystal alloy, such as a single-crystal nickel superalloy embodied as a turbine blade or other turbine engine component. In yet another embodiment, the test body 10 may include a composite material, such as a polymer matrix composite reinforced with fibers (e.g., carbon fibers) or a metal matrix composite (e.g., an aluminum alloy matrix reinforced with silicon carbide and/or other types of fibers). In yet a further embodiment, the test body 10 may include a single-crystal semiconductor substrate, such as a single-crystal silicon wafer, a single-crystal gallium arsenide wafer, or other single-crystal semiconductor wafer.

In at least one embodiment, the nondestructive testing system 100 may determine onset of failure of the test body 10 due to material separation in an alloyed material. For example, the controller 130 may be calibrated by testing calibration test bodies that include alloyed material susceptible to separation of alloying constituents (e.g., 5000 series Aluminum alloys; as discussed above, the magnesium aluminide, such as beta phase ($Mg_2Al_3$), may separate from aluminum-magnesium alloy within the 5000 series Aluminum; beta phase corrosion/separation in titanium alloys; hydrogen embrittlement and/or sensitization in titanium alloys; etc.). Moreover, multiple calibration tests may be conducted and corresponding data may be stored for test bodies at various degrees or states of alloying material separation (e.g., experimental data on beta phase separation testing of 5456 Aluminum alloy is provided below). Hence, in some embodiments, readings or signals produced by the light detector 120 in response to irradiating the respective test bodies may be correlated by the controller 130 to the beta phase separation in the 5000 series aluminum.

In some embodiments, when the nondestructive testing system 100 tests the test body 10, the controller 130 may determine the level of separation of alloying material from base material. For example, when the nondestructive testing system 100 tests the test body 10, the controller 130 may determine the level of the separation of the alloying material in the test body 10. Moreover, as mentioned above, the controller 130 may include various threshold values and/or ranges for material separation (e.g., precipitation of one or more intermetallic compounds at or near grain boundaries), which may correspond to an indication or recommendation provided by the controller 130. In an embodiment, when the signal received from the light detector 120 is at or near a threshold value or within a threshold range (or corresponds to alloying material separation of a threshold value or range), the controller 130 may provide an indication on whether the test body 10 may be placed back into service. For example, when the level of alloying material separation is at or near a distinct threshold value or within a threshold range, the controller 130 may provide one or more corresponding indications or recommendations (e.g., to repeat test within T period of time, to monitor operation of the test body, to remove and/or replace or repair the test body, etc.).

As described above, the controller 130 may include input/output interface. In an embodiment, an output device 140, such as a computer display, may be coupled to the controller 130 (e.g., at the input/output interface of the controller 130). Furthermore, an input device (e.g., a keyboard, mouse, microphone, etc.) may be coupled to the controller 130 at the input/output interface and may receive input from a user (as mentioned above). For example, a user may provide input related to the type of material that comprises the test body 10, the surface finish of the test body 10, etc. In an embodiment, the output displayed from the controller 130 may be at least partially based on the input provided at the input/output interface (e.g., user input), signal(s) received from the light detector 120, and the calibration data, as described above. It should be also appreciated that the controller 130 may be calibrated by a user or by a manufacturer. Moreover, in some embodiments, a single controller may be calibrated by performing the calibration tests, and the calibration data may be used on or exported to any number of additional controller in any number of nondestructive testing systems (e.g., with or without additional calibration testing).

In some embodiments, the controller 130 may include or store signal threshold data for identifying or correlating signal(s) received from the light detector 120 to a strain or fatigue levels predictive of imminent or upcoming failure of the test body 10 (e.g., the threshold strain and/or fatigue values provided by user may be correlated or mapped to a corresponding signal value that would be received from the light detector 120). For example, the controller 130 may compare the signal received from the light detector 120 to the signal threshold value(s) or threshold ranges and may provide an indication or recommendation related to further use of the test body 10 (e.g., whether to remove the test body 10 from service).

In one or more embodiments, the controller 130 may include or store threshold value(s) and/or threshold ranges related to a change in signal received from light detector 120. In particular, for example, the nondestructive testing system 100 may test the test body 10 in a first test (e.g., before the test body 10 is placed in service) and may, subsequently, test the test body 10 in a second test (e.g., after a test body 10 has been in service for a period of time), and the controller 130 may compare the signal(s) received from the light detector 120 in the first test to the signal(s) received from the light detector 120 in the second test. Furthermore, the controller 130 may compare the difference in the signal(s) from the first test and signal(s) from the second test to one or more threshold values or threshold ranges related to the change in signal. The threshold value for change in the signal may correspond to one or more fatigue and/or strain states and may correspond to one or more indications or recommendations generated by the controller, such as to remove the test body 10 from service, to retest the test body 10 at a later time, etc. For example, when the change in the signal between the first and second tests is equal to or greater than a threshold value (or within a range of threshold values), the controller 130 may generate an output or recommendation (e.g., which may be displayed on the display) that indicates whether the test body 10 should be taken out of service.

In some embodiments, the controller 130 may be calibrated to include or store data related to probabilities of failure of the test body 10 during operation, which may correspond to signal(s) received from the light detector 120. For example, the probability of failure due to fatigue and/or strain may be related to the material of the test body 10, geometry of the test body 10, strain and/or fatigue level(s), operating conditions (e.g., load experienced by the test body 10, frequency of cycles, environmental parameters, such as temperature, etc.). Moreover, the probability of failure may be expressed in terms of time or duration of continuous operation of the test body 10 (e.g., the probability that the test body 10 may remain in service without failure for T time periods, for T+1 time periods, for T+2 time periods, etc.).

The controller 130 may be calibrated to include one or more values of operating conditions that may be predictive of the probability of failure of the test body 10 that correspond with the calibration signal(s) (or signal values) received from the light detector 120 and/or change in signal received from the light detector 120 in multiple tests of the test body 10. For example, the controller 130 may be calibrated by: (i) providing or entering in the controller 130 one or more values of operating conditions of a calibration test body (that may be the same or similar to the test body 10); (ii) testing the calibration test body with the nondestructive testing system 100 and storing the signal values received from the light detector 120; and (iii) placing the test body 10 back in service and recording the number of time periods of continuing operation of the test body 10 and/or the number of loading cycles and/or load experience by the test body 10 before failure to correspond with the stored signal(s).

Additionally or alternatively, the controller 130 may be calibrated by: (i) providing or entering in the controller 130 one or more values of operating conditions of a calibration test body (that may be analogous to the test body 10); (ii) testing the calibration test body in two or more calibration tests and storing the values related to the change in signal received from the light detector 120 in different tests; and (iii) placing the test body 10 back in service and recording the number of time periods of continuing operation of the test body 10 and/or the number of loading cycles and/or load experience by the test body 10 before failure to correspond with the stored values related to the change in signal(s). In some embodiments, after calibrating, the nondestructive testing system 100 may test the test body 10, and the controller 130 may provide one or more probabilities that the test body 10 may continue operating without failure (e.g., the controller 130 may provide corresponding probabilities of continuous operation of test body 10 for T time periods, T+1 periods, T+2 periods, etc.).

Figure 2:
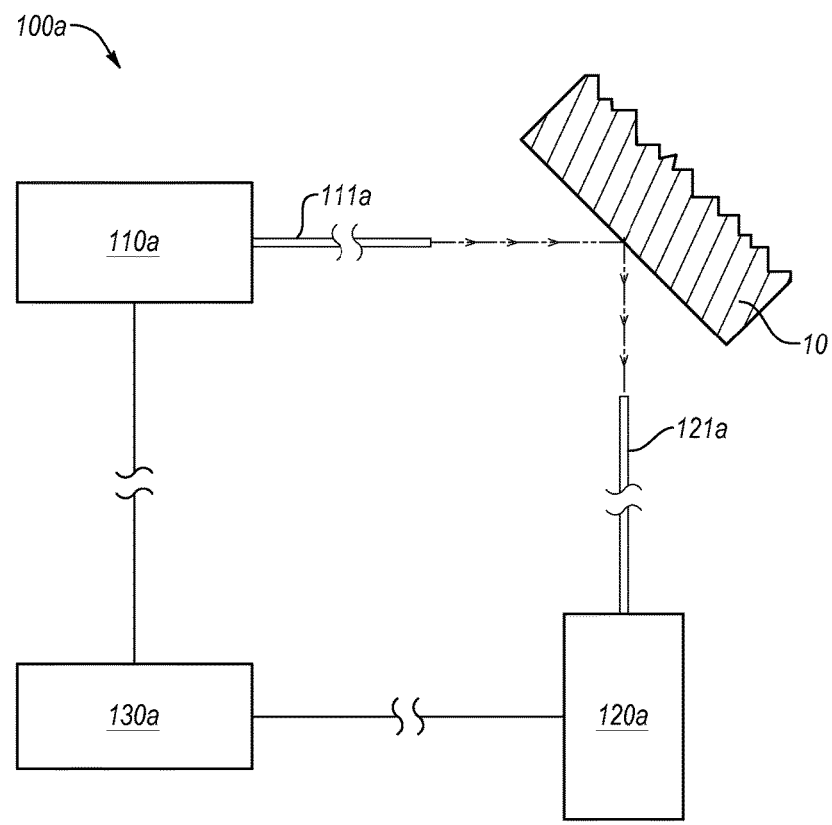
FIG. 2 illustrates a nondestructive testing system that includes a light source and light detector positioned distally from a test body, according to an embodiment.

In some embodiments, the light source and/or the photodetector of the nondestructive testing system may be positioned remotely from the test body. FIG. 2 illustrates a nondestructive testing system 100a that includes a light source 110a and light detector 120a positioned distally from the test body 10, according to an embodiment. Except as described herein, the nondestructive testing system 100a and its elements and components may be similar to or the same as the nondestructive testing system 100 (FIG. 1).

For example, the nondestructive testing system 100a may include optical fibers 111a and 121a respectively optically coupled to the light source 110a and light detector 120a. In particular, respective ends of the optical fibers 111a and 121a may be positioned at or near the surface of the test body 10, while the light source 110a and/or the light detector 120a may be positioned at any number of suitable locations. For example, as described above, the light source 110a may include a laser (e.g., a high power laser, such as q-switching laser), which may be positioned in a building, in a vehicle, etc., and the optical fiber 111a may extend from the light source 110a to a location near the surface of the test body 10. In an embodiment, the light detector 120a also may be positioned remotely from the test body 10 (e.g., in a building, in a vehicle, etc.). In some embodiments, the light source 110a may be integrated with the optical fiber 111a (e.g., a fiber laser).

In some embodiments, the nondestructive testing system 100a may include controller 130a (e.g., similar to or the same as the controller 130 (FIG. 1)). For example, the controller 130a may be coupled to the light detector 120a.

Generally, the controller 130a may be positioned at any suitable location relative to the light detector 120a. In an embodiment, the controller 130a may be coupled to and/or may direct operation of the light source 110a. For example, the controller 130a may turn the light source 110a on and/or off. In some embodiments, the controller 130a may control power of the light source 110a. For example, the intensity of light emitted from the light source 110a may be suitable or sufficient for detection at the light detector 120a but below a threshold power value (e.g., the intensity of light irradiating the test body 10 may be such as to limit or prevent damage to the surface of the test body 10 by the light emitted from the light source 110a).

In some embodiments, the nondestructive testing system 100a may scan along the surface of the test body 10. For example, the nondestructive testing system 100a may test the test body 10 at multiple locations on the surface of the test body 10 (e.g., locations where the light from the light source 110a impinges onto the surface of the test body 10). Moreover, the location where the light impinges on the surface of the test body 10 may be changed or advanced (e.g., automatically, manually, etc.), such as to test multiple locations (e.g., along a line, along multiple lines or in a grid pattern, etc.). In an embodiment, the controller 130a may control or direct advancement or movement of the optical fibers 111a and/or 121a, thereby moving the where location the light emitted from the light source 110a impinges onto the surface of the test body 10. For example, the optical fibers 111a and 121a may be held in a fixture at predetermined orientation relative to each other and to the surface of the test body 10 as well as at predetermined distance from the surface of the test body 10.

The controller 130a may direct advancement or movement of the optical fibers 111a and/or 121a (e.g., by advancing or moving a fixture securing the optical fibers 111a an 121a). In some embodiments, the controller 130a may be coupled to an optical sensor or detector (e.g., to a camera or a machine vision system) that may provide an image of the surface of the test body 10 to the controller 130a. For example, the controller 130a may map test locations on the surface of the test body 10 based at least partially on the image provided from the optical sensor. Furthermore, the controller 130a may control or direct movement of the optical fibers 111a and/or 121a, such that the light emitted from the light source 110a and received at the light detector 120a impinges onto the surface of the test body 10 at mapped locations that correspond to the mapped locations on the image received from optical sensor.

In some embodiments, the test body 10 and the optical fibers 111a and/or 121a may be rotated relative to each other (e.g., by rotating the test body 10 and/or optical fibers 111a and/or 121a), such that the surface location of the test body 10 is tested at various angles. For example, the test body 10 may be rotated about a rotation axis that is generally perpendicular to surface of the test body 10 at the test location and in a manner that the test location remains generally the same at various rotation positions (e.g., the rotation axis may generally pass through the test location). For example, testing the location on the surface of the test body 10 at various angles (as the test body is rotated about the rotation axis) may facilitate obtaining a better signal reading from the light detector 120a, which may reduce effects of surface roughness on the signal (e.g., the controller 130a may average out the signals received from the light detector 120a when testing the test body 10 at various angles). It should be also appreciated that the test body 10 may be rotated relative to the light source 110 and light detector 120 of the nondestructive testing system 100 (FIG. 1) in the same manner.

Moreover, the test surface of the test body 10 may be prepared for testing by producing a suitable surface roughness thereof. For example, the inventors found that a surface roughness of a ground sample (e.g., about 0.1 μm Ra to about 1.6 μm Ra) produces a suitable or sufficient amount of second harmonic generation light. It should be appreciated, however, that the test surface of the test body 10 may have surface roughness that is greater than 1.6 μm Ra or less than 0.1 μm Ra.

Figure 3:
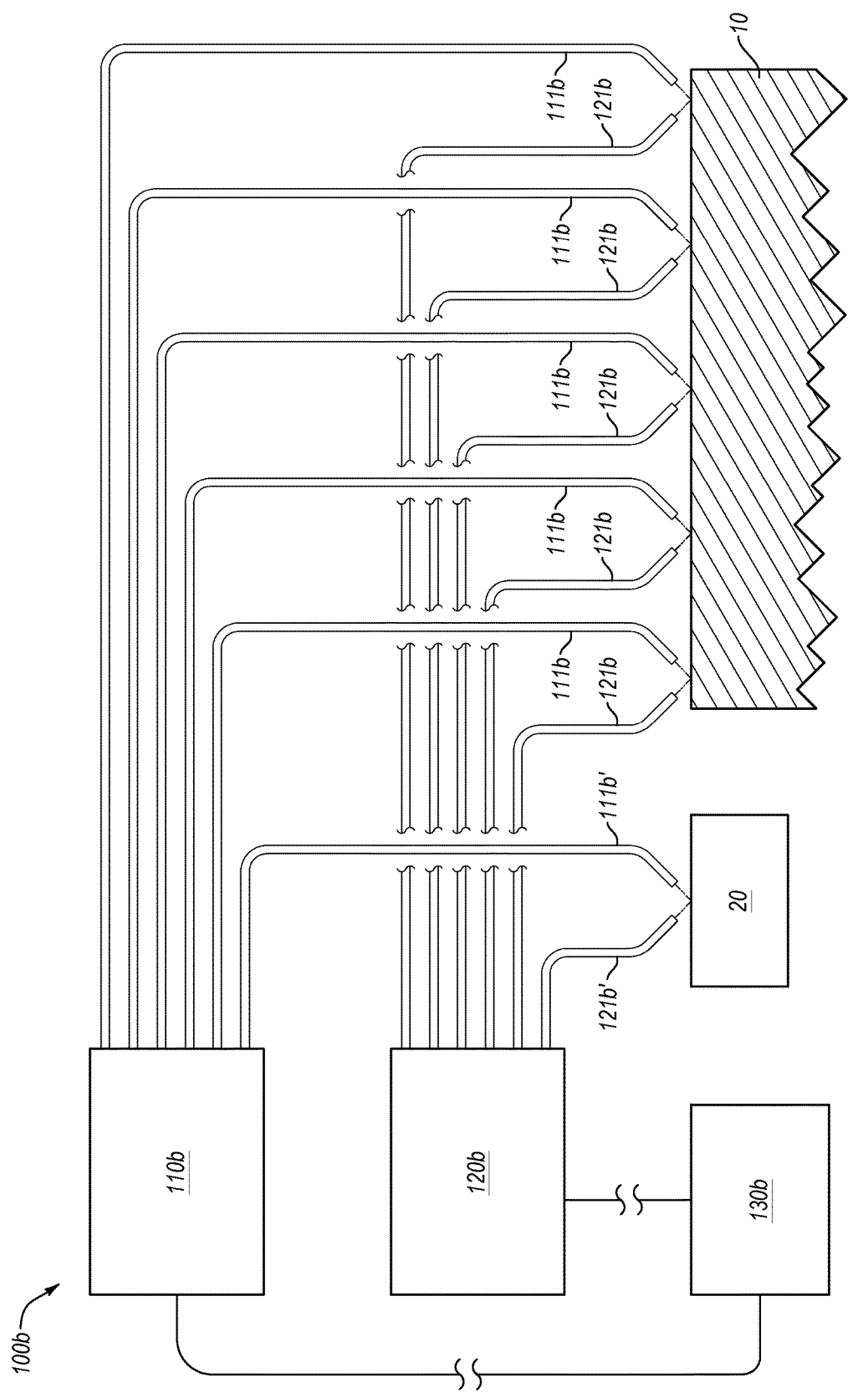
FIG. 3 illustrates a nondestructive testing system that includes multiple optical fibers coupled to a light source and multiple optical fibers coupled to a light detector, according to an embodiment.

It should be appreciated that the nondestructive testing system may include any number of optical fibers coupled to the light source and any number of optical fibers coupled to the light detector. FIG. 3 illustrates a nondestructive testing system 100b that includes multiple optical fibers 111b coupled to a light source 110b and multiple optical fibers 121b coupled to a light detector 120b of the nondestructive testing system 100b, according to an embodiment. Except as otherwise described herein, the nondestructive testing system 100b and its elements and components may be similar to or the same as any of the nondestructive testing systems 100, 100a (FIGS. 1-2). In an embodiment, the nondestructive testing system 100b may include a controller 130b that may be coupled to the light source 110a and/or to the light detector 120a (e.g., as described above).

In some embodiments, the multiple optical fibers 111b and 121b may be positioned in order to test or probe the surface of the test body 10 at multiple locations. For example, the nondestructive testing system 100b may test multiple locations on the surface of the test body 10 simultaneously or substantially simultaneous. In an embodiment, the controller 130b may control operation of the light source 110b and/or switching between the optical fibers 111b, such that the nondestructive testing system 100b may include a single light source 110b and a single light detector 120b (e.g., the optical fibers 111b may be coupled to a single light source 110b and the controller 130b may direct or control switching among the optical fibers 111b, such that one or more predetermined optical fibers 111b are activated). Hence, the light sensed at the light detector 120b may be attributed to a particular location or position on the surface of the test body 10, which corresponds with the location of the activated optical fibers 111b. Additionally or alternatively, in some embodiments, the controller 130b may receive signal based on the amount of light received and/or detect by the light detector 120b from multiple 121b at multiple locations (e.g., the controller 130b may determine an average signal by dividing the total value of signal received by the number of location from which the light was received at the light detector 120b).

As described above, the nondestructive testing system 100b may scan or test surface of the test body 10 at multiple locations. For example, the multiple optical fibers 111b and 121b may be arranged at predetermined distances and/or positions (e.g., in a linear arrangement) from one another and may be collectively advanced over the surface of the test body 10. Moreover, as the controller 130b receives signal values from the light detector 120b for corresponding locations on the surface of the test body 10, the in controller 130b may determine one or more locations that have strain and/or fatigue above a threshold value and/or within a threshold range of values.

In some embodiments, the controller 130b may compare signal(s) received from the light detector 120b to one or more signals received from one or more corresponding control test bodies, such as control test body 20 (e.g., optical fiber 111b' may be coupled to the light source 110b and may guide the light therefrom to the surface of the control test body 20, and optical fiber 121b' may guide the second frequency light from the control test body 20 to the light detector 120b). The control test body 20 may have a predetermined and/or known strain and/or fatigue level (e.g., annealed, strained below a threshold value, strained at or above a threshold value, etc.). In an embodiment, a user may enter or provide the known value of the strain or fatigue of the control test body 20 to the controller 130b. Additionally or alternatively, the control test body 20 may be at a threshold value of strain or fatigue. For example, a signal received from the light detector 120b when testing a location on the surface of the test body 10 that is the same as or sufficiently similar to the signal received from the light detector 120b when testing the surface of the control test body 20 may indicate that the test body 10 at the tested location may be compromised and/or the test body 10 may be unsuitable for further service.

Figure 4:
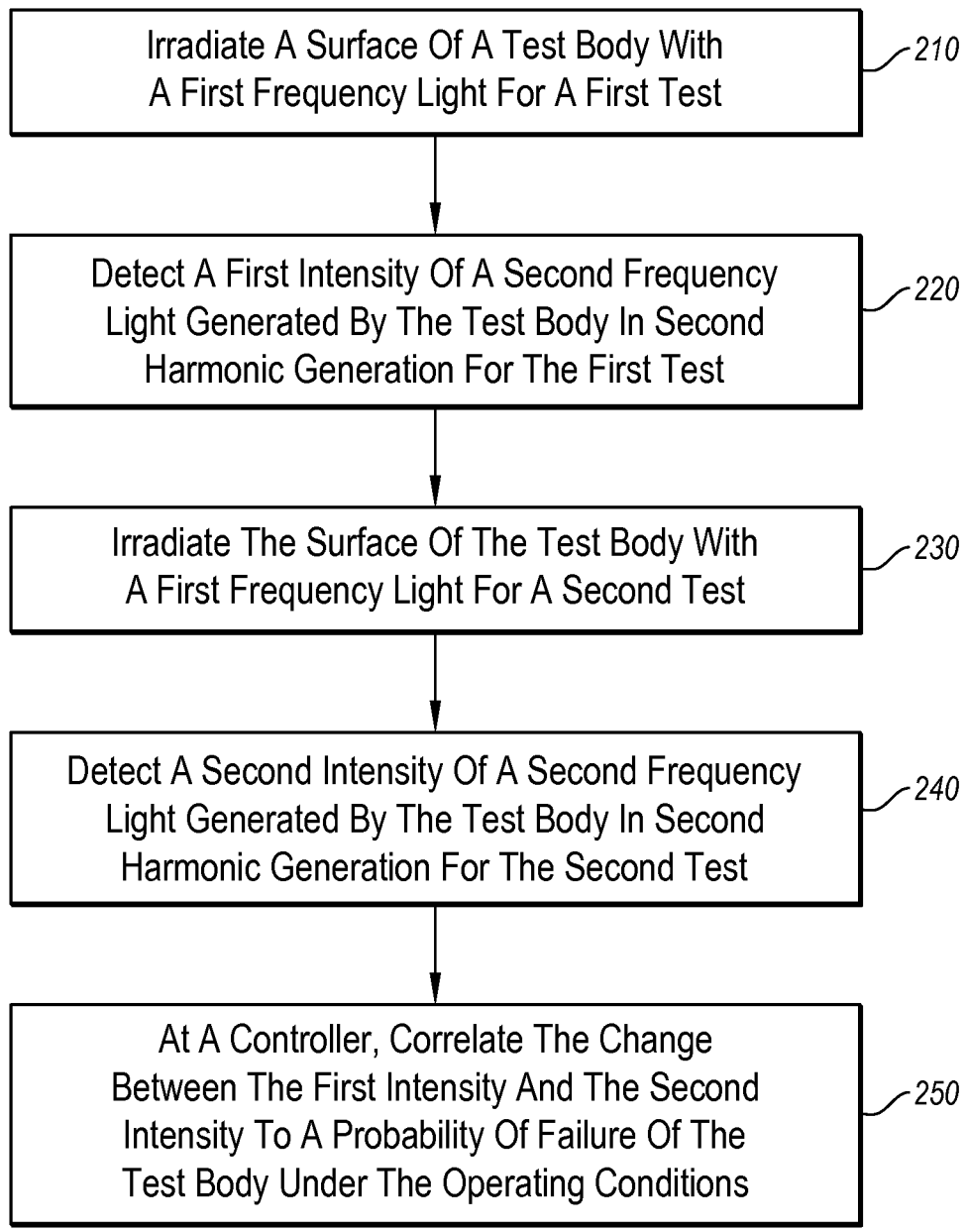
FIG. 4 is a flow chart of a method of nondestructively testing a test body according to an embodiment.

As mentioned above, the nondestructive testing system may determine whether to remove or to recommend removal of the test body out of service. In an embodiment, the test body may be initially tested in a first test and may be subsequently tested in a second test (e.g., after a time period, after a number of loading cycles, etc.). FIG. 4 is a flow chart of a method of nondestructively testing a test body according to an embodiment. It should be appreciated that any of the nondestructive testing systems 100, 100a, 100b (FIGS. 1-3) may be used to test the test body according to the method described below.

For example, for the first test, the testing method may include an act 210 of irradiating a surface of a test body with a predominately first frequency light and an act 220 of detecting a first intensity of a predominately second frequency light generated by the test body in second harmonic generation. Furthermore, for the second test, the method may include an act 230 of irradiating the surface of the test body with the predominately first frequency light and an act 240 of detecting a second intensity of a predominately second frequency light generated by the test body in second harmonic generation. Moreover, the method may include an act 250 of correlating a change between the first intensity (from the first test) and the second intensity (from the second test) to a probability of failure of the test body under operating conditions. For example, the act 250 may be performed by one of the controllers, as described above. It should be also appreciated that in the first test, the test body may be a control test body (e.g., as described above, a test body with known or measured level of strain, fatigue, material degradation or separation, such as beta phase separation, etc.). Hence, in some embodiments, the signals obtained from testing the control test body in the first test may be compared to the signals obtained from testing the test body in the second test.

EXPERIMENTAL DATA

Test 1—Testing 5456 Aluminum Alloy for Beta Phase Separation

Three samples were tested using a nondestructive testing system similar to the system 100 shown in FIG. 1. The three samples included (1) an Annealed sample that had no or very little beta phase separation; (2) an Intermediate sample that has some beta phase separation but at a level that would not affect usability of the material in operation (having a Degree of Sensitization (DOS) of 6 mg/cm$^2$); and (3) a Sensitized sample having DOS of 40 mg/cm$^2$, which would lead to degradation of the mechanical strength of the material. The signals received from the light detector were as follows: (1) for Annealed sample, the signal was about 3.347; (2) for the Intermediate sample the signal was about 4.395; and (3) for the Sensitized sample, the signal was about 7.110.

Test 2—Testing 2024 Aluminum Alloy for SHG Signal Response to Extension Deformation To determine the relationship between the change in the signal received from the light detector (detecting the second harmonic generation light emitted from a test sample of 2024 Aluminum Alloy), the test sample was loaded to produce extension thereof. The samples at various levels of deformation were tested using a nondestructive testing system similar to the system 100 shown in FIG. 1. The results are provided in the table below, where the extension is indicated in mm, the load is in N, and the signal was measured in V/S.

| Extension (mm) | Load (N) | Signal Change (V/s) |
| --- | --- | --- |
| 0.202 | 518.196 | 1.366 |
| 0.387 | 1003.025 | −1.161 |
| 0.768 | 1366.560 | −4.422 |
| 0.809 | 1430.006 | −4.110 |
| 0.970 | 1447.954 | −7.779 |

While various aspects and embodiments have been disclosed herein, other aspects and embodiments are contemplated. The various aspects and embodiments disclosed herein are for purposes of illustration and are not intended to be limiting.

What is claimed is:
1. A nondestructive material testing system, comprising:
a light source configured to emit predominantly a first frequency light and configured to irradiate a portion of a surface of a test body at a first location;
a light detector positioned and configured to detect an intensity of a second frequency light that is emitted from the test body in second harmonic generation responsive to the first frequency light; and
a controller coupled to the light detector and configured to:
receive at least one baseline value from the light detector corresponding to an amount of light detected by the light detector from the test body while the light source does not emit the first frequency of light;
receive one or more first signal values from the light detector, the one or more first signal values corresponding to an amount of the second frequency light detected by the light detector from the test body;
filter out the at least one baseline value from the first signal value; and
output one or more of a probability of failure of the test body under operating conditions at least partially based on the one or more first signal values or a recommendation on placing the test body into service at least partially based on the one or more first signal values.
2. The nondestructive material testing system of claim 1, wherein the controller includes calibration data that includes one or more probabilities correlated with one or more calibration signal values, the one or more probabilities corresponding with one or more of a number of cycles to failure or a period of time in operation to failure; and the probability of failure of the test body under operating conditions is based at least partially on correlating the one or more calibration signal values with the one or more first signal values.

3. The nondestructive material testing system of claim 1, wherein:

the controller includes calibration data that includes one or more calibration signal values corresponding to levels of fatigue or strain in material of the test body; and the recommendation on placing the test body into service is based at least partially on correlating the one or more calibration signal values with the one or more first signal values.

4. The nondestructive material testing system of claim 3, wherein the controller includes one or more threshold values corresponding to one or more of fatigue or strain of the material of the test body, and the recommendation is based at least partially on the one or more threshold values.

5. The nondestructive material testing system of claim 1, wherein:

the controller includes calibration data that includes one or more calibration signal values corresponding to levels of beta phase in material of the test body; and one or more of the probability of failure of the test body under operating conditions or the recommendation on placing the test body into service is based at least partially on comparison of the one or more calibration signal values and the one or more first signal values.

6. The nondestructive material testing system of claim 1, further comprising an optical filter positioned between the light detector and the surface of the test body, the optical filter configured to at least partially filter out the first frequency light from passing therethrough to the light detector.

7. The nondestructive material testing system of claim 1, further comprising one or more of at least one light source optical fiber coupled to the light source, the at least one light source optical fiber positioned and oriented to irradiate the portion of the surface of the test body; or at least one light detector optical fiber coupled to the light detector, the at least one light detector optical fiber positioned and oriented to receive the second frequency light that is emitted from the test body.

8. The nondestructive material testing system of claim 7, wherein:

the at least one light source optical fiber includes multiple light source optical fibers, at least one of the multiple light source optical fibers is positioned and oriented to irradiate a surface of a control test body;

the at least one light detector optical fiber includes multiple light detector optical fibers, at least one of the multiple light detector optical fibers is positioned and oriented to receive the second frequency light emitted from the control test body;

the controller is configured to receive a control signal value received from the light detector, the control signal value corresponding to the amount of the second frequency light detected by the light detector from the control test body; and the recommendation on placing the test body into service is based at least partially on a comparison of the control signal value to the one or more first signal values.

9. The nondestructive material testing system of claim 7, wherein:

the at least one light source optical fiber includes multiple light source optical fibers, at least one of the multiple light source optical fibers is positioned and oriented to irradiate the surface of the test body at the first location and at least one other one of the multiple light source optical fibers is positioned and oriented to irradiate the surface of the test body at a second location, different from the first location; and the at least one light detector optical fiber includes multiple light detector optical fibers, at least one of the multiple light detector optical fibers is positioned and oriented to receive the second frequency light emitted from the test body at the first location and at least another one of the multiple light detector optical fiber is positioned and oriented to receive the second frequency light emitted from the test body at the second location.

10. The nondestructive material testing system of claim 1, wherein the light detector includes one or more of a photomultiplier tube or a photodiode.

11. A nondestructive material testing system, comprising:

a light source positioned at a first location, the light source configured to emit predominantly a first frequency light and further configured to irradiate a portion of a surface of a test body;

a light detector positioned and configured to detect an intensity of a second frequency light that is emitted from the test body in second harmonic generation responsive to the first frequency light; and a controller coupled to the light detector, the controller including calibration data that includes one or more calibration signal values corresponding to changes in material structure, the controller configured to:

receive a first signal value from the light detector corresponding to an amount of the second frequency light detected by the light detector from the test body during a first test;

receive a second signal value from the light detector corresponding to an amount of the second frequency light detected by the light detector from the test body during a second test; and determine one or more of a probability of failure of the test body under operating conditions or a recommendation on placing the test body into service based at least partially on a comparison of the one or more calibration signal values and a difference between the first signal value and the second signal value.

12. The nondestructive material testing system of claim 1, wherein the controller is further configured to output one or more of the probability of failure of the test body under operating conditions or the recommendation on placing the test body into service.

13. The nondestructive material testing system of claim 1, further comprising an optical filter positioned between the light detector and the surface of the test body, the optical filter configured to at least partially filter out the first frequency light from passing therethrough to the light detector.

14. The nondestructive material testing system of claim 1, further comprising one or more of at least one light source optical fiber coupled to the light source, the at least one light source optical fiber positioned and oriented to irradiate the portion of the surface of the test body; or at least one light detector optical fiber coupled to the light detector, the at least one light detector optical fiber positioned and oriented to receive the second frequency light that is emitted from the test body.

15. The nondestructive material testing system of claim 14, wherein:
the at least one light source optical fiber includes multiple light source optical fibers, at least one of the multiple light source optical fibers is positioned and oriented to irradiate the surface of the test body at the first location and at least one other of the multiple light source optical fibers is positioned and oriented to irradiate the surface of the test body at a second location that is different from the first location; and
the at least one light detector optical fiber includes multiple light detector optical fibers, at least one of the multiple light detector optical fibers is positioned and oriented to receive the second frequency light emitted from the test body at the first location and at least another one of the multiple light detector optical fibers is positioned and oriented to receive the second frequency light emitted from the test body at the second location.

16. The nondestructive material testing system of claim 11, wherein the one or more calibration signal values corresponding to levels of separation of one or more alloying constituents in the material of the test body.

17. A method for predicting failure of a test body under operating conditions, the method comprising:
irradiating a surface of a test body at a first location with predominately a first frequency light for a first test;
responsive to irradiating the surface of the test body at the first location with predominately the first frequency light, detecting a first intensity of a second frequency light generated by the test body in second harmonic generation for the first test;
irradiating the surface of the test body at a second location with predominately the first frequency light for a second test;
responsive to irradiating the surface of the test body at the second location with the first frequency light, detecting a second intensity of the second frequency light generated by the test body in second harmonic generation for the second test;
at a controller including calibration data, outputting one or more of a probability of failure of the test body under the operating conditions or a recommendation on placing the test body into service at least partially based on a comparison of one or more calibration signal values of the calibration data and a change between the first intensity and the second intensity, wherein the one or more calibration signal values correspond to a change in material structure.

18. The method of claim 17, where the first location is generally the same as the second location.

19. The method of claim 17, where the first location is different from the second location.

20. The method of claim 17, wherein the controller includes calibration data related to strain of the test body for the first test or for the second test.

21. The method of claim 17, wherein the controller includes calibration data related to dislocation density in the test body for one or more of the first test or for the second test.

* * * * *